(12) United States Patent
Schwartz et al.

(10) Patent No.: US 11,333,434 B1
(45) Date of Patent: May 17, 2022

(54) FABRIC WARMING RACK

(71) Applicants: Joseph Schwartz, Hollywood, FL (US); Gunter Felix, Hialeah, FL (US)

(72) Inventors: Joseph Schwartz, Hollywood, FL (US); Gunter Felix, Hialeah, FL (US)

(73) Assignee: SPA WORLD CORPORATION, Miami, FL (US)

( * ) Notice: Subject to any disclaimer, the term of this patent is extended or adjusted under 35 U.S.C. 154(b) by 0 days.

(21) Appl. No.: 17/095,041

(22) Filed: Nov. 11, 2020

(51) Int. Cl.
  *F26B 25/18* (2006.01)
  *F21V 33/00* (2006.01)
  *F21Y 115/10* (2016.01)

(52) U.S. Cl.
  CPC .......... *F26B 25/18* (2013.01); *F21V 33/0044* (2013.01); *F21Y 2115/10* (2016.08)

(58) Field of Classification Search
  CPC ...... F26B 25/18; F21V 33/0044; F21V 23/06; F21Y 2115/10; H02B 45/20; H05B 45/10
  USPC ........................................................ 219/385
  See application file for complete search history.

(56) References Cited

U.S. PATENT DOCUMENTS

| 8,096,062 | B1 | 1/2012 | Bellen |
| 8,143,553 | B2 | 3/2012 | DeFranco et al. |
| 2010/0148090 | A1 | 6/2010 | Chang |
| 2011/0259864 | A1 | 10/2011 | Galietti |
| 2011/0305597 | A1* | 12/2011 | Farren ............ A61L 2/10 422/24 |
| 2013/0153560 | A1* | 6/2013 | Lev ............ H05B 3/06 219/385 |
| 2013/0214174 | A1 | 8/2013 | Domenig et al. |

FOREIGN PATENT DOCUMENTS

| CN | 201542535 U | 8/2010 |
| CN | 105662254 A | 6/2016 |
| CN | 107198483 A | 9/2017 |
| CN | 108420349 A | 8/2018 |
| CN | 209770207 U | 12/2019 |
| CN | 110876575 A | 3/2020 |
| CN | 105286704 A | 6/2020 |
| KR | 200342825 Y1 | 2/2004 |

OTHER PUBLICATIONS

International Search Report and Written Opinion issued in International Application No. PCT/US2020/060008 dated Feb. 12, 2021.

* cited by examiner

*Primary Examiner* — Andrew J Coughlin
*Assistant Examiner* — Jessica M Apenteng
(74) *Attorney, Agent, or Firm* — Mark H. Francis; Heath M. Sargeant; Holland & Knight LLP

(57) ABSTRACT

A fabric warming rack comprises a rod extending along a horizontal plane and a first light source rotatably coupled to the rod and configured to rotate about the rod.

20 Claims, 13 Drawing Sheets

FABRIC WARMING RACK

TECHNICAL FIELD

The present disclosure generally relates to fabric warming racks and, more particularly, for unenclosed fabric warming racks.

BACKGROUND

Warm and sterile towels are not only desirable to have after bathing or showering, but may be required in a medical environment. It is well known that a warmed towel serves to offset the chilling effect due to evaporation of water from the body after showering, even at normal room temperatures.

With the rise of antibiotic resistant bacteria and other pathogens, cleanliness is of the utmost importance. Sterilizing a towel or fabric is the best way to ensure that there are no pathogens on a surface that is going to be in direct bodily contact. If a towel contaminated with a dangerous virus or bacteria came in contact with several individuals, the potential for the spread of disease is greatly increased. The soothing feeling that a warm towel provides after a bath or shower is positive reinforcement to a user to continue using warmed towels on a regular basis. By combining a sterilizing feature, a user will benefit from a clean sterile towel free of dangerous bacteria and other pathogens. Unfortunately, at this time there are no devices that both warm and disinfect towels that are adaptable to home or commercial use.

While a number of apparatus have been proposed for this purpose, all of them have many disadvantages. These disadvantages include complexity, expense, and bulky enclosures as well as the inability to satisfactorily sterilize a towel or other fabric. Prior art towel warmers require enclosures and the placement of towels or other fabrics within the enclosure for a predefined period of time. Once these towels are warmed and sanitized, they would have to be transported to where a user would need them.

For example, the "Towel Drying System" of U.S. Pat. No. 8,096,062 includes a rigid housing, a blower pulling air into the housing, and a towel support member for holding towels. The disadvantages of this device include the required housing, the inclusion of a blower, and considerable weight and size.

In another example, the "Digital Auto Hot Towel Cabinet Systems" of U.S. Patent Application Publication No. 2011/0259864 similarly requires a cabinet (e.g., a frame with a door hingedly coupled to the frame). The disadvantages of this device also include the required cabinet, complex operating controls, and considerable weight and size.

In yet another example, the "Multi-purpose Ultraviolet Sterilizer" of U.S. Patent Application Publication No. 2010/0148090 also requires an enclosure (e.g., a body having six planes with one of the planes being a door). As with the other prior art, the disadvantages of this device include the required enclosure, complex operating controls, and considerable weight and size.

Even in the case of the "Ultraviolet sterilized towel rack" of Chinese Patent No. 105286704, this solution positions an ultraviolet disinfection lamp with a reflector in parallel with a towel bar such that the ultraviolet disinfection lamp and reflector may be oriented between a vertical surface of the towel bar and less than 90 degrees from the vertical surface of the towel bar. The disadvantages with this device include the manual orienting of the ultraviolet disinfection lamp and reflector and the inconsistent emission of ultraviolet light along the length of a towel hanging from the towel bar.

In light of the prior art, it may be beneficial to warm and sanitized towels or other fabrics without requiring an additional, enclosed appliance in a way that will ensure sanitizing of an entire towel or fabric.

SUMMARY

In an embodiment, a fabric warming rack includes a rod extending along a horizontal plane and a first light source rotatably coupled to the rod and configured to rotate about the rod.

One or more of the following features may be included. The first light source may include one or more ultraviolet (UV) light sources. A first reflector assembly may be rotatably coupled to the rod and configured to reflect at least a portion of light emitted by the first light source toward the rod. A second light source may be positioned on a first end of the rod. A third light source may be positioned on a second end of the rod. The second light source may extend along a vertical plane relative to the rod. The third light source may extend along a vertical plane relative to the rod. The second light source may include one or more ultraviolet (UV) light sources. The third light source may include one or more ultraviolet (UV) light sources. A first reflector assembly may be positioned on the first end of the rod and configured to reflect at least a portion of light emitted by the first light source toward the rod. A second reflector assembly may be positioned on the second end of the rod and configured to reflect at least a portion of light emitted by the second light source toward the rod. The fabric warming rack may include one or more of a wall-mounting assembly and a ground-mounting assembly. The fabric warming rack may be unenclosed.

According to another embodiment, a fabric warming rack may include a rod extending along a horizontal plane. A first light source may be rotatably coupled to the rod and configured to rotate about the rod. A second light source may be positioned at a fixed vertical distance from the rod.

One or more of the following features may be included. At least one of the first light source and the second light source includes one or more ultraviolet (UV) light sources. A first reflector assembly may be rotatably coupled to the rod and configured to reflect at least a portion of light emitted by the first light source toward the rod. A second reflector assembly may be rotatably coupled to the rod and configured to reflect at least a portion of light emitted by the second light source toward the rod. A third light source may be positioned on a first end of the rod. A fourth light source positioned on a second end of the rod. The third light source may extend along a vertical plane relative to the rod. The fourth light source may extend along a vertical plane relative to the rod. The fabric warming rack may include one or more of a wall-mounting assembly and a ground-mounting assembly. The fabric warming rack may be unenclosed.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF EXAMPLE EMBODIMENTS

In general, consistent with the present disclosure, a fabric warming rack is provided. For example, and referring generally to FIGS. 1-9, in some embodiments, a fabric warming rack may include at least one rod extending along a horizontal plane, a first light source positioned on a first end of the at least one rod, and a second light source positioned on a second end of the at least one rod. As will be discussed in greater detail below, embodiments of the present disclosure may allow for fabrics, such as towels, placed on an unenclosed drying rack to be warmed and sanitized evenly across the fabric. In this manner, the light from the light sources (e.g., ultraviolet light sources) may be evenly distributed across a fabric hanging on a drying rack rod.

Figure 1:
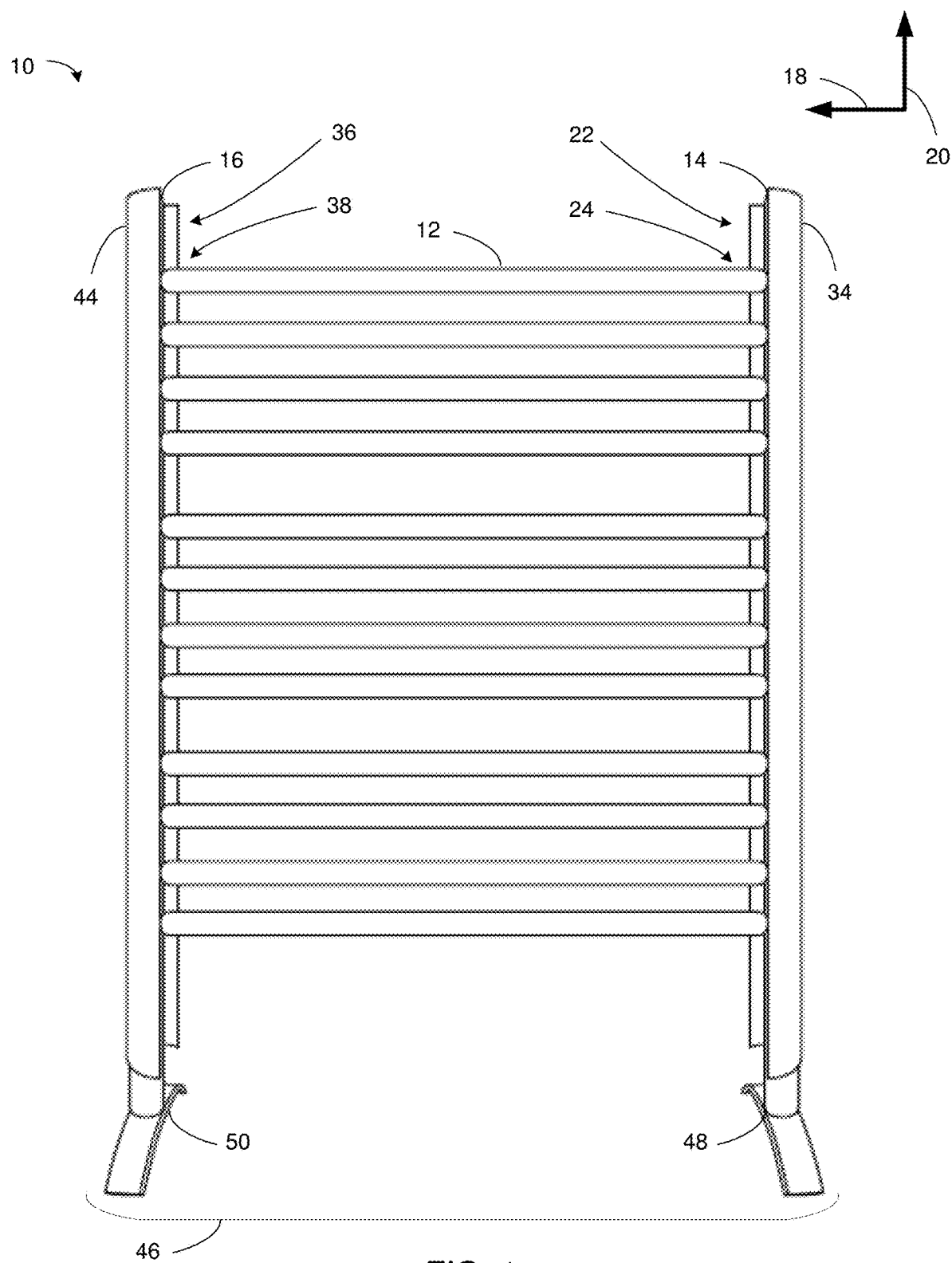
FIG. 1 is a front elevation view of a fabric warming rack, according to an example embodiment.
Figure 2:
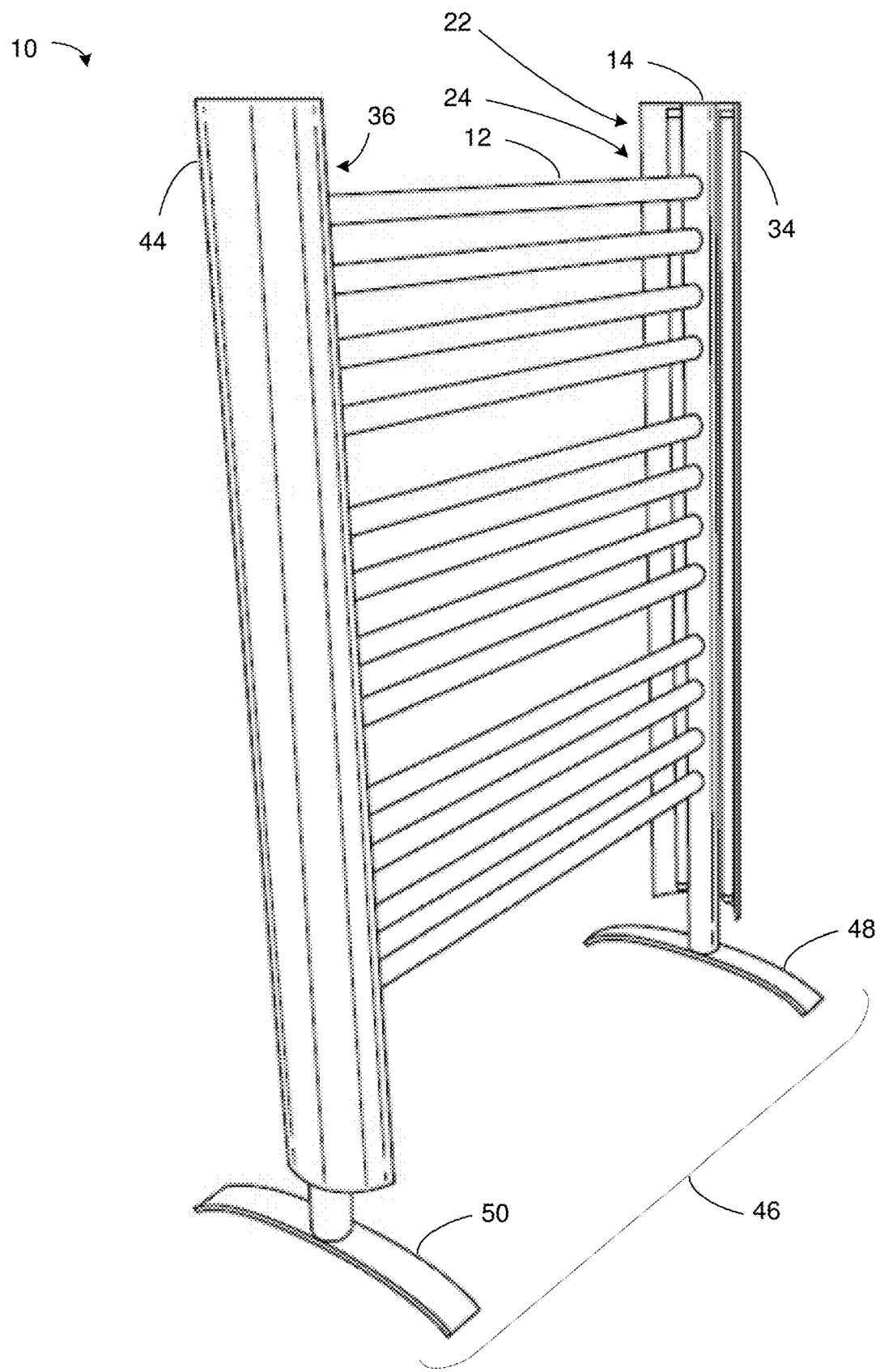
FIG. 2 is a perspective view of a fabric warming rack, according to various example embodiments.

Referring to FIGS. 1-5 and in some implementations, an unenclosed fabric warming rack (e.g., fabric warming rack 10) may include at least one rod (e.g., at least one rod 12) extending along a horizontal plane between a first support member (e.g., first support member 14) and a second support member (e.g., second support member 16). For example, fabric warming rack 10 may include at least one rod 12 positioned between first support member 14 and second support member 16. In this manner, at least one rod 12 may be configured for draping a fabric on fabric warming rack 10. As will be discussed in greater detail below, a draped fabric (e.g., a towel) may be evenly warmed and sanitized while placed on fabric warming rack 10. While the example of FIGS. 1-2 show three groups of four rods extending between the first support member and the second support member, it will be appreciated that any number of rods may be used within the scope of the present disclosure.

In some implementations, at least one rod 12 may be any structural member extending along a horizontal plane (i.e., in the direction of arrow 18) between at least two supporting structures (e.g., first support member 14 and/or second support member 16). However, it will be appreciated that at least one rod 12 may extend in any direction within the scope of the present disclosure. In some implementations, the at least two support structures may extend along a vertical plane (i.e., in the direction of arrow 20). However, it will be appreciated that the at least two support structures may extend in any direction within the scope of the present disclosure.

In some implementations, the at least one rod may be generally cylindrical or tubular to allow fabrics to be draped along a curved surface of at least one rod 12. In this manner, a fabric may be draped on and removed from at least one rod 12 with limited friction across the at least one rod. For example, after a period of warming and sanitizing, a user may remove a fabric from fabric warming rack 10 by pulling on a draped portion of the fabric. Because of the curved surface of at least one rod 12, a fabric may be removed with minimal force and without potentially damaging or snagging the fabric. While an example of a generally cylindrical or tubular rod has been discussed, it will be appreciated that any shape or surface pattern for the at least one rod may be used within the scope of the present disclosure.

In some implementations, at least a portion of at least one rod 12 may include a textured surface configured to provide additional surface friction. For example, the textured surface (e.g., a coating) of at least one rod 12 may provide sufficient friction between a fabric draped on the rod and the surface of the rod to maintain the fabric on the rod until a sufficiently strong force is applied to the fabric to pull the fabric off of the at least one rod. While an example of a textured surface configured to provide increased friction has been provided, it will be appreciated that a surface coating may be applied to reduce friction between the fabric and the at least one rod as a user pulls the fabric off of the rod.

In some implementations, at least one rod 12 may be formed of various materials known in the art (e.g., metals, thermally-conductive materials, metal-alloys, etc.). Additionally, first support member 14 and/or second support member 16 may be formed of the same material(s) as at least one rod 12 or from different material(s).

Figure 3:
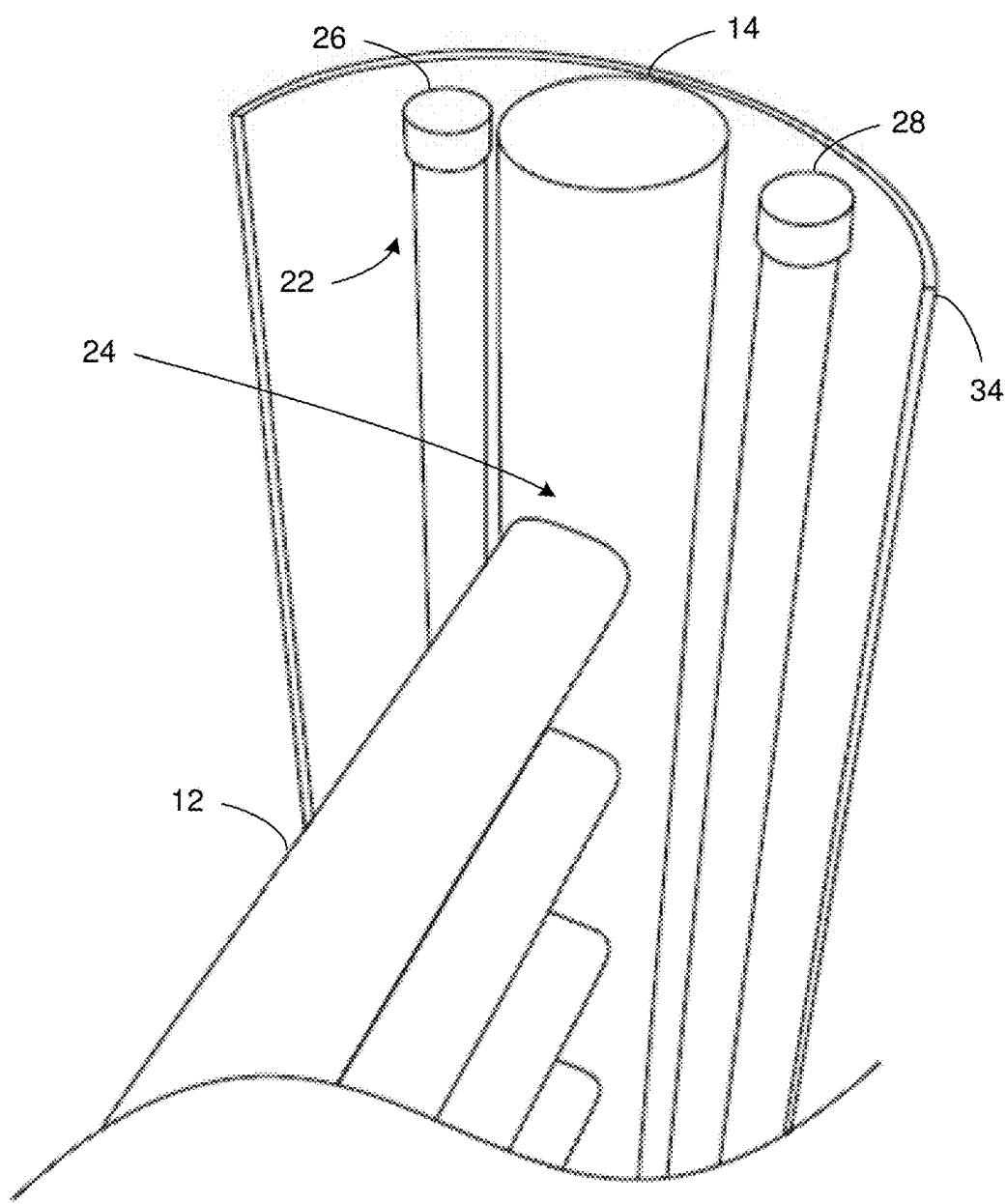
FIG. 3 is a diagrammatic view of a first light source and a first reflector assembly, according to various example embodiments.
Figure 4:
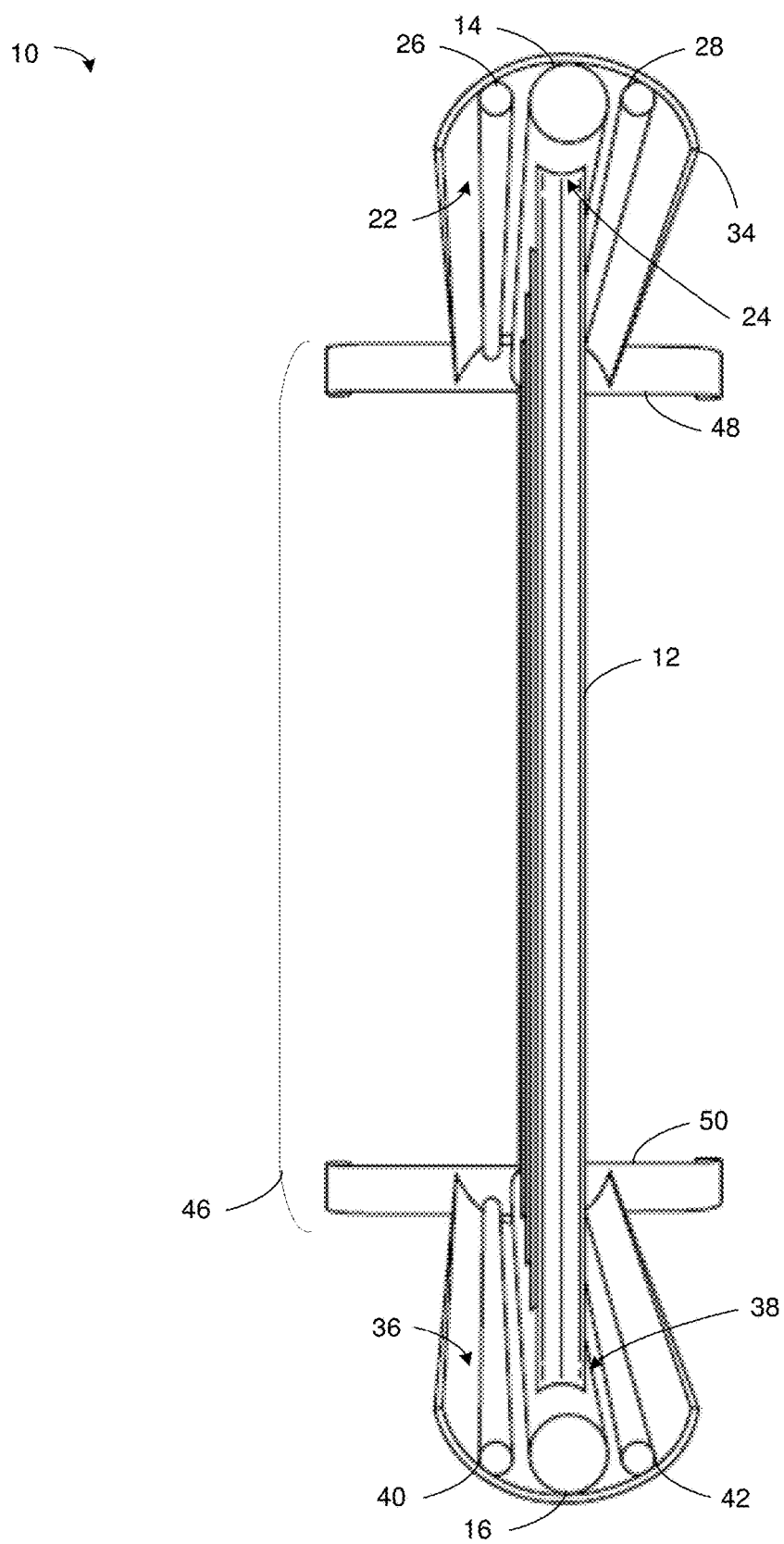
FIGS. 4-5 are top views of a fabric warming rack, according to various example embodiments.
Figure 5:
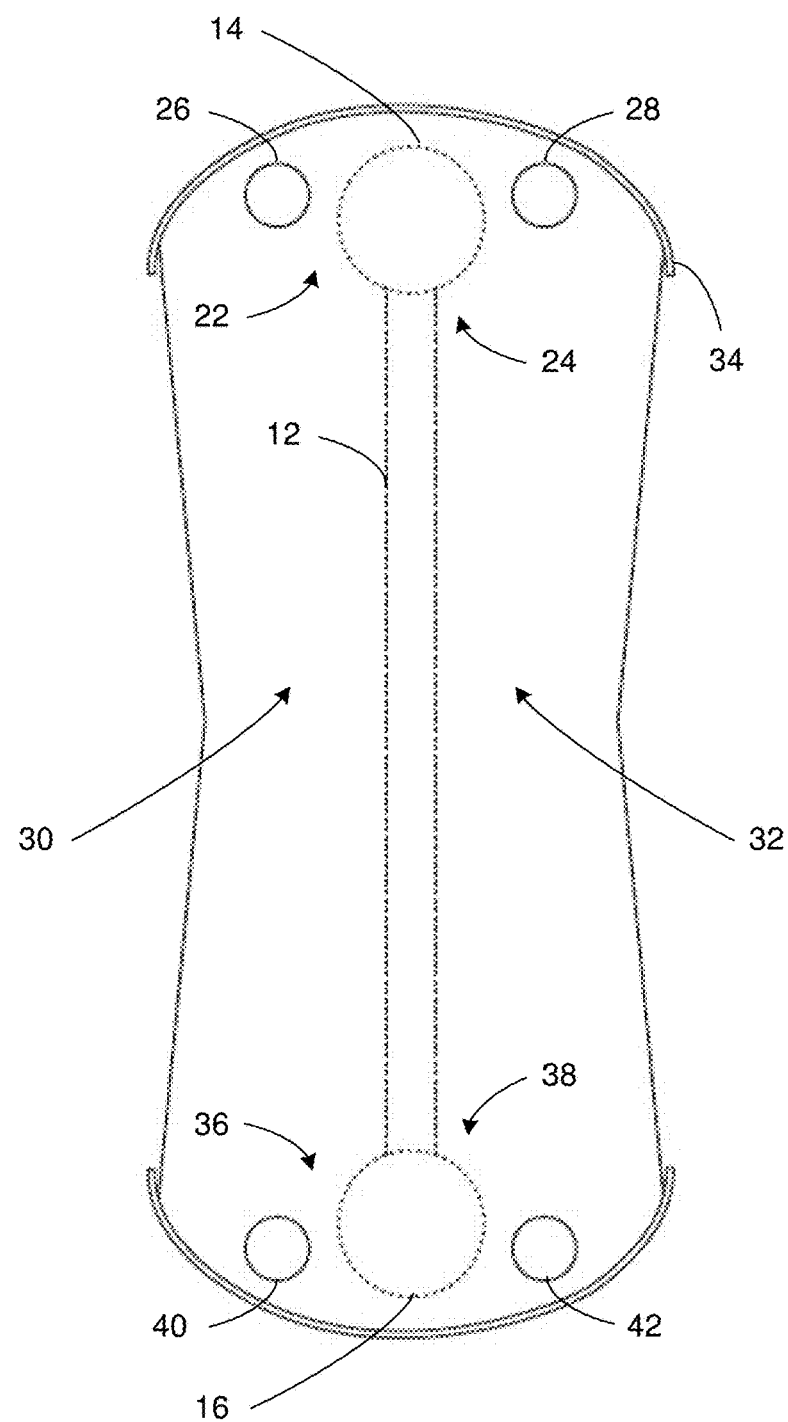

Referring also to the examples of FIGS. 3-5 and in some implementations, unenclosed fabric warming rack 10 may include a first light source positioned on a first end of the at least one rod. A light source may include any assembly or structure configured to produce light. In some implementations, a light source may include a lighting assembly configured to control the light produced by one or more lights (e.g., lamps, light bulbs, light emitting diodes (LEDs), etc.). In this manner, a light source may include an assembly or structure with or without lights (e.g., light bulbs, light emitting diodes, etc.). For example and as shown in FIG. 3, a first light source (e.g., first light source 22) may be positioned on a first end (e.g., first end 24) of at least one rod (e.g., at least one rod 12). In some implementations, positioning the first light source (e.g., first light source 22) on the first end (e.g., first end 24) of the at least one rod (e.g., at least one rod 12) may include positioning the first light source (e.g., first light source 22) adjacent to the first end (e.g., first end 24) of the at least one rod (e.g., at least one rod 12). As shown in the example of FIG. 3, first light source 22 may generally extend along a vertical plane relative to the at least one rod (e.g., in the direction of arrow 20 which is perpendicular to at least one rod 12). However, it will be appreciated that the first light source (e.g., first light source 22) may be positioned on the first end (e.g., first end 24) of the at least one rod (e.g., at least one rod 12) in various non-perpendicular configurations or orientations relative to the at least one rod within the scope of the present disclosure.

In some implementations, the first light source may extend at least partially along a first support member. For example and referring again to the example of FIG. 2, first light source 22 may extend along the length of first support member 14. In this manner and as will be discussed in greater detail below, first light source 22 may emit light along the entire length of first support member 14 toward at least one rod 12. In some implementations, first light source 22 may include a plurality of lights sources distributed along the length of first support member 14.

In some implementations, first light source 22 may include one or more infrared light sources. As is known in the art, an infrared light source or infrared lamp emits infrared radiation. In this manner, infrared light sources may warm or heat fabric placed on fabric warming rack 10. While an example of infrared light sources has been provided, it will be appreciated that various combinations of light sources may be used within the scope of the present disclosure.

For example and in some implementations, the first light source may include one or more ultraviolet (UV) light sources. As is known in the art, UV is a form of electromagnetic radiation that can sterilize exposed areas. Referring again to the example of FIGS. 3 and 5 and in some implementations, first light source 22 may include a pair of UV light sources (e.g., UV light sources 26, 28) positioned on first end 24 of at least one rod 12 and extending along the length of first support member 14. In this example, UV light sources 26, 28 may be positioned on opposite sides of first support member 14 and configured to emit UV light on both sides of at least one rod 12. In this manner and as will be discussed in greater detail below, UV light sources 26, 28 may warm and sterilize fabric draped on both sides of at least one rod 12 (i.e., a portion of fabric on a first side (e.g., first side 30) of at least one rod 12 and a portion of fabric on a second side (e.g., second side 32) of at least one rod 12. In some implementations, UV light sources 26, 28 may be directed UV light sources (i.e., configured to emit UV light in a certain direction) and/or undirected UV light sources (i.e., configured to emit UV light in every direction).

In some implementations and as shown in the example of FIG. 3, UV light sources 26, 28 may be elongated, tubular or cylindrical UV light assemblies extending along first support member 14. However, it will be appreciated that UV light sources 26, 28 may include discrete UV light sources positioned along first support member 14 and/or positioned at first end 24 of at least one rod 12. It will also be appreciated that the discrete UV light sources may be configured to operate independently of one another. For example, a plurality of light emitting diode (LED) strips may be used as UV light sources within the scope of the present disclosure and that each LED strip may be used independently of any other LED strip.

Referring again to the example of FIG. 2 and in some implementations, suppose fabric warming rack 10 includes three groups of four rods. In this example, a first UV light source may be positioned on the first end of the first group of four rods; a second UV light source may be positioned on the first end of the second group of four rods; and a third UV light source may be positioned on the first end of the third group of four rods. While an example with e.g., three groups of e.g., four rods has been described, it will be appreciated that any number of groups of rods or UV light sources on any end of the fabric warming rack may be used within the scope of the present disclosure.

Referring again to the example of FIG. 3 and as discussed above, first light source 22 may emit light in many directions. For example, suppose first light source 22 includes a pair of UV light sources (e.g., UV light sources 26, 28). In this example, suppose UV light sources 26, 28 are elongated tubular light bulbs which are configured to emit light radially outwards. As portions of this radiated light is not oriented towards at least one rod 12, the efficiency of first light source 22 as a warming and sanitizing source may be limited.

Referring also to the example of FIG. 5 and in some implementations, fabric warming rack 10 may include a first reflector assembly positioned on the first end of the at least one rod and configured to reflect at least a portion of light emitted by the first light source toward the at least one rod. For example, a first reflector assembly (e.g., first reflector assembly 34) may be positioned on the first end (e.g., first end 24) of the at least one rod (e.g., at least one rod 12) and configured to reflect at least a portion of light emitted by the first light source (e.g., first light source 22) toward the at least one rod. In the example of FIG. 5, first reflector assembly 34 may be a curved metal or other material known in the art that is configured to reflect light emitted from first light source 22 back to at least one rod 12. While in this example, first reflector assembly 34 may be curved, it will be appreciated that first reflector assembly 34 may be configured in various shapes and forms within the scope of the present disclosure. As shown in the example of FIG. 5, light emitted by first light source 22 may be either directly emitted or reflectively emitted toward at least one rod 12. In this manner, fabric warming rack 10 may allow fabrics to be evenly warmed and sanitized.

In some implementations, first reflector assembly 34 may be integrally formed with first support member 14 and/or coupled to first support member 14. In some implementations, first light source 22 may be coupled to or integrally formed with first reflector assembly 34. In this manner, reflection of light back directly toward first light source 22 may be minimized. In some implementations, first reflector assembly 34 may be configured to extend along at least a portion of the length of first support member 14. Referring again to the example of FIG. 2, first reflector assembly 34 may be configured to extend along the length of first support member 14 and may be as equal in length to, longer than, or shorter than first light source 22. As discussed above and in some implementations, first reflector assembly 34 may include one or more reflector subassemblies corresponding to different groupings of rods of fabric warmer rack 10. Accordingly, it will be appreciated that first reflector assembly is not limited to an individual reflector assembly within the scope of the present disclosure.

In some implementations, fabric warming rack 10 may include a second light source positioned on a second end of the at least one rod. For example and as discussed above relative to the first light source, fabric warming rack 10 may include a first light source positioned on a first end of the at least one rod. For example and as shown in FIG. 4, a second light source (e.g., second light source 36) may be positioned on a second end (e.g., second end 38) of at least one rod (e.g., at least one rod 12). In some implementations, positioning second light source 36 on the second end 38 of the at least one rod 12 may include positioning second light source 36 adjacent to second end 38 of the at least one rod 12. For example and as shown in the example of FIG. 4, second light source 36 may generally extend along a vertical plane relative to the at least one rod generally perpendicular to at least one rod 12. However, it will be appreciated that second light source 36 may be positioned on second end 38 of at least one rod 12 in various non-perpendicular configurations or orientations relative to the at least one rod within the scope of the present disclosure.

In some implementations, the second light source may extend at least partially along a second support member. For example and referring again to the example of FIG. 4, second light source 36 may extend along the length of second support member 16. In this manner and as will be discussed in greater detail below, second light source 36 may emit light along the entire length of second support member 16 toward at least one rod 12. In some implementations and as discussed above relative to the first light source, second light source 36 may include a plurality of lights sources distributed along the length of second support member 16.

In some implementations and as discussed above relative to first light source 22, second light source 36 may include one or more infrared light sources configured to warm fabrics positioned on fabric warming rack 10. For example and in some implementations, the second light source may include one or more ultraviolet (UV) light sources. Referring again to the example of FIG. 4 and in some implementations, second light source 36 may include a pair of UV light sources (e.g., UV light sources 40, 42) positioned on second end 38 of at least one rod 12 and extending along the length of second support member 16. In this example, UV light sources 40, 42 may be positioned on opposite sides of second support member 16 and configured to emit UV light on both sides of at least one rod 12. In this manner and as will be discussed in greater detail below, UV light sources 40, 42 may warm and sterilize fabric draped on both sides of at least one rod 12 (i.e., a portion of fabric on a first side (e.g., first side 30) of at least one rod 12 and a portion of fabric on a second side (e.g., second side 32) of at least one rod 12. In some implementations, UV light sources 40, 42 may be directed UV light sources (i.e., configured to emit UV light in a certain direction) and/or undirected UV light sources (i.e., configured to emit UV light in every direction).

In some implementations, the first light source (e.g., first light source 22) and the second light source (e.g., second light source 36) may include identical light sources. Referring again to the example of FIG. 4, first light source 22 positioned on first end 24 may include UV light sources 26, 28 and second light source 36 positioned on second end 38 may also include UV light sources 40, 42. In some implementations, the first light source (e.g., first light source 22) and the second light source (e.g., second light source 36) may include different light sources. For example, first light source 22 positioned on first end 24 may include UV light sources 26, 28 and second light source 36 positioned on second end 38 may include non-UV light sources 40, 42. In some implementations, each of the first light source (e.g., first light source 22) and the second light source (e.g., second light source 36) may include different types of light sources (e.g., one or more UV light sources, one or more infrared light sources, etc.).

In some implementations, fabric warming rack 10 may include a second reflector assembly positioned on the second end of the at least one rod and configured to reflect at least a portion of light emitted by the second light source toward the at least one rod. For example, a second reflector assembly (e.g., second reflector assembly 44) may be positioned on the second end (e.g., second end 38) of the at least one rod (e.g., at least one rod 12) and configured to reflect at least a portion of light emitted by the second light source (e.g., second light source 36) toward the at least one rod. In the example of FIG. 5, second reflector assembly 44 may be a curved metal or other material known in the art that is configured to reflect light emitted from second light source 36 back to at least one rod 12. While in this example, second reflector assembly 44 may be curved, it will be appreciated that second reflector assembly 44 may be configured in various shapes and forms within the scope of the present disclosure. As shown in the example of FIG. 5, light emitted by second light source 36 may be either directly emitted or reflectively emitted toward at least one rod 12. In this manner, fabric warming rack 10 may allow fabrics to be evenly warmed and sanitized.

In some implementations, second reflector assembly 44 may be integrally formed with second support member 16 and/or coupled to second support member 16. In some implementations, second light source 36 may be coupled to or integrally formed with second reflector assembly 44. In this manner, reflection of light back directly toward second light source 36 may be minimized. In some implementations, second reflector assembly 44 may be configured to extend along at least a portion of the length of second support member 16. Referring again to the example of FIG. 1, second reflector assembly 44 may be configured to extend along the length of second support member 16 and may be as equal in length to, longer than, or shorter than second light source 36. As discussed above and in some implementations, second reflector assembly 44 may include one or more reflector subassemblies corresponding to different groupings of rods of fabric warmer rack 10. Accordingly, it will be appreciated that second reflector assembly is not limited to an individual reflector assembly within the scope of the present disclosure.

In some implementations, fabric warming rack 10 may be unenclosed. For example and as discussed above, conventional approaches for warming and sanitizing fabrics require enclosed housings. Referring again to the example of FIG. 5 and in some implementations, with a first light source in combination with a first reflector assembly on a first end of at least one rod and a second light source in combination with a second reflector assembly on a second end of the at least one rod, a fabric draped on the at least one rod may be warmed and sanitized evenly without requiring an enclosure. In this manner, fabric warming rack 10 may be unenclosed and utilized in environments where towel racks may be located (e.g., in bathrooms, spas, swimming pools, etc.).

In some implementations and as is known in the art, a power source for fabric warming rack 10 may be provided by an external connection or an integral power source within fabric warming rack 10. For example and in some implementations, a power source for the first light source and second light source may include a power cable extending along a portion of one or more of the first support member and/or the second support member. In some implementations, fabric warming rack 10 may include an external power switch configured to switch power on and off to the first light source and the second light source. In some implementations, fabric warming rack 10 may include a first power switch for the first light source and a second power switch for the second light switch. While an example with two power switches has been provided, it will be appreciated that any number of power switches may be used within the scope of the present disclosure.

For example, fabric warming rack 10 may include one or more power switches or controls to activate one or more light sources to warm a fabric and one or more power switches or controls to activate one or more UV light sources to sanitize the fabric. In this manner, fabric warming rack 10 may be configured (e.g., by operation of the one or more power switches or controls) to warm and/or sanitize a fabric positioned on the rack. In some implementations, the one or more power switches or controls may activate the warming light sources and UV light sources together. In some implementations, fabric warming rack 10 may include one or more timers for controlling the one or more warming light sources and/or the one or more UV light sources. In this manner, fabric warming rack 10 may provide safety controls for the warming and/or sanitizing of fabrics. In some implementations, each timer may include a default maximum amount of "on" time. For example, a timer configured to activate one or more warming light sources may include a timer that automatically shuts off the one or more warming light sources after a threshold amount of time. The threshold amount of time may be user-defined or a default, pre-programmed value. Additionally, fabric warming rack 10 may include a time that automatically shuts off the one or more UV lights sources after a threshold amount of time. In some implementations, the threshold amount of time may be different for the one or more warming light sources versus the one or more UV light sources. In some implementations, each timer may include the same threshold amount of time before shutting down light sources.

In some implementations, fabric warming rack 10 may include one or more resistive warming elements within the at least one rod. For example, in addition to the first light source positioned on the first end and the second light source positioned on the second end, fabric warming rack may include one or more resistive warming elements integrated within the at least one rod. In this manner, the one or more resistive warming elements within the at least one rod may provide heat to an interior portion surface of a fabric positioned on the at least one rod and the first light source and/or the second light source may provide warming and/or sanitization of the external surface of the fabric.

In some implementations, fabric warming rack 10 may be configured to be electrically coupled to a power source by hardwiring (e.g., a fixed electrical connection to a stationary power source), a removable plug, and/or connection to a battery or other rechargeable power supply.

Referring again to the examples of FIGS. 1, 2, and 4 and in some implementations, fabric warming rack 10 may include a ground-mounting assembly. For example, fabric warming rack 10 may be configured to be a free-standing rack assembly supported by a ground-mounting assembly (e.g., ground mounting assembly 46). In some implementations, ground-mounting assembly 46 may be placed on the ground or removably secured or anchored to the ground. In some implementations, ground-mounting assembly 46 may include one or more ground-mounting subassemblies. For example and as shown in FIGS. 1, 2, and 4, a first ground-mounting subassembly (e.g., first ground mounting subassembly 48) may be coupled to a first support member (e.g., first support member 14) and a second ground-mounting subassembly (e.g., second ground-mounting subassembly 50) may be coupled to a second support member (e.g., second support member 16). While an example with two ground-mounting subassemblies has been discussed, it will be appreciated that ground-mounting assembly 46 may include any number of ground-mounting subassemblies within the scope of the present disclosure.

Figure 6:
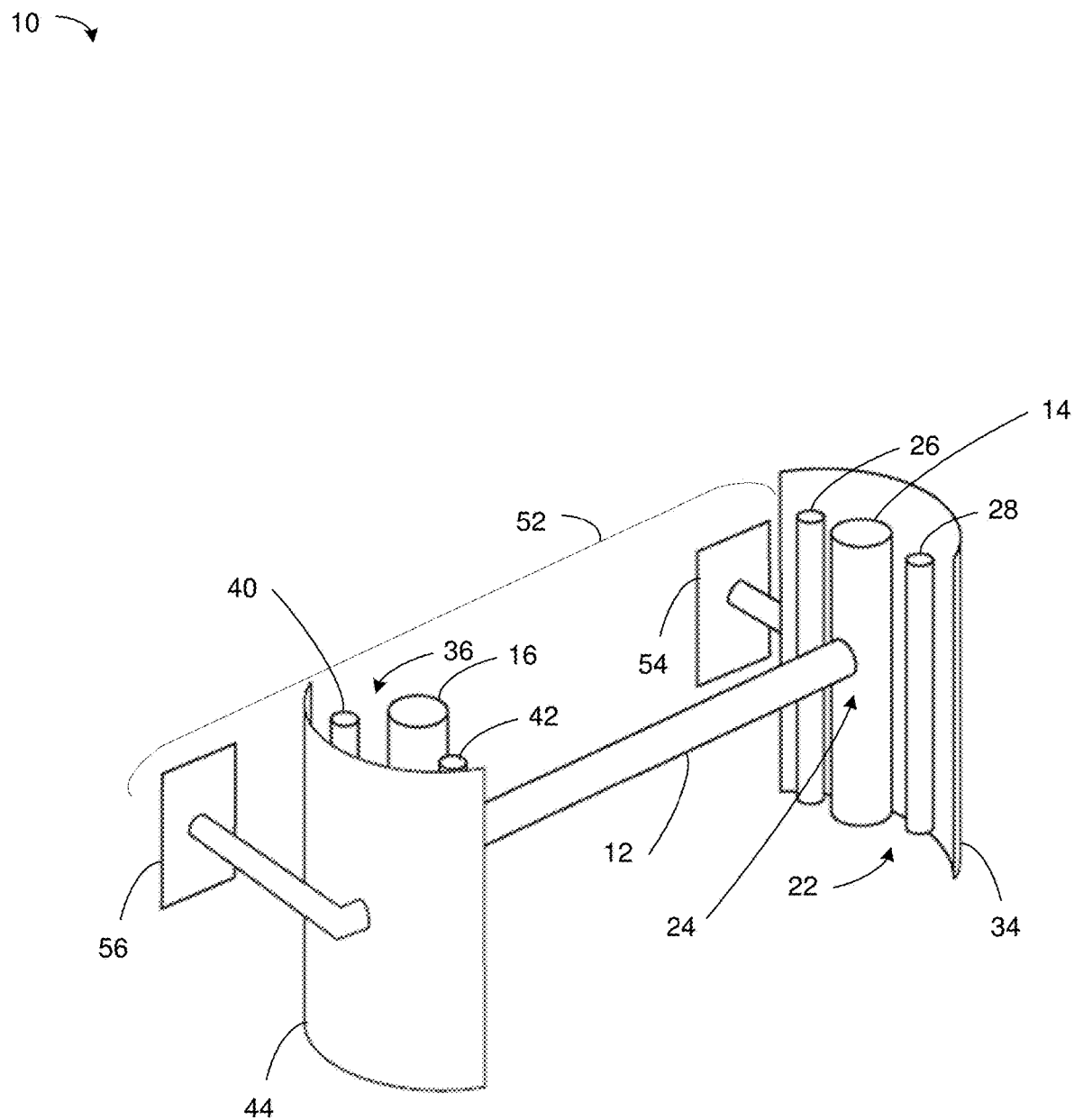
FIGS. 6-9 are diagrammatic views of wall-mounted fabric warming racks, according to various example embodiments.

Referring also to the example of FIGS. 6-9 and in some implementations, fabric warming rack 10 may include a wall-mounting assembly. In some implementations and as shown in the example of FIG. 6, a wall-mounting assembly (e.g., wall-mounting assembly 52) may include a first wall-mounting subassembly (e.g., first wall-mounting sub-assembly 54) coupled to the first reflector assembly (e.g., first reflector assembly 34) and a second wall-mounting assembly (e.g., second wall-mounting assembly 56) coupled to the second reflector assembly (e.g., second reflector assembly 44).

Figure 7:
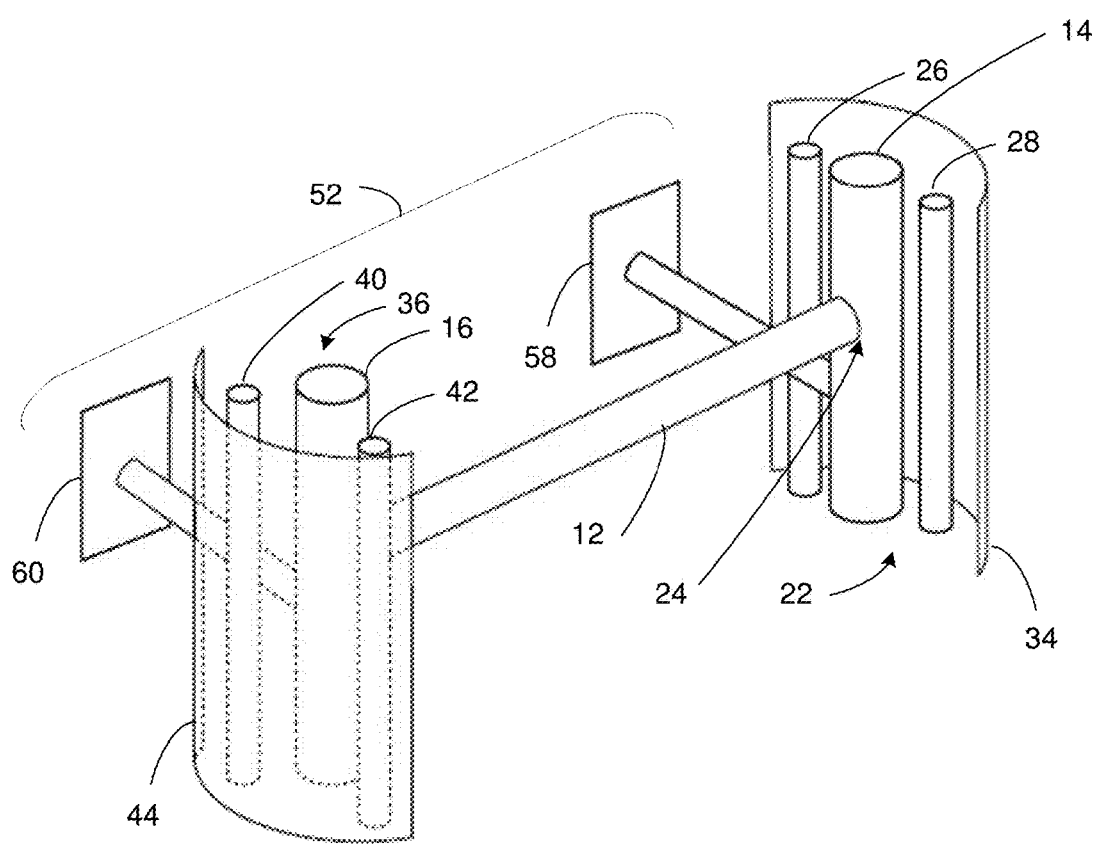
Figure 8:
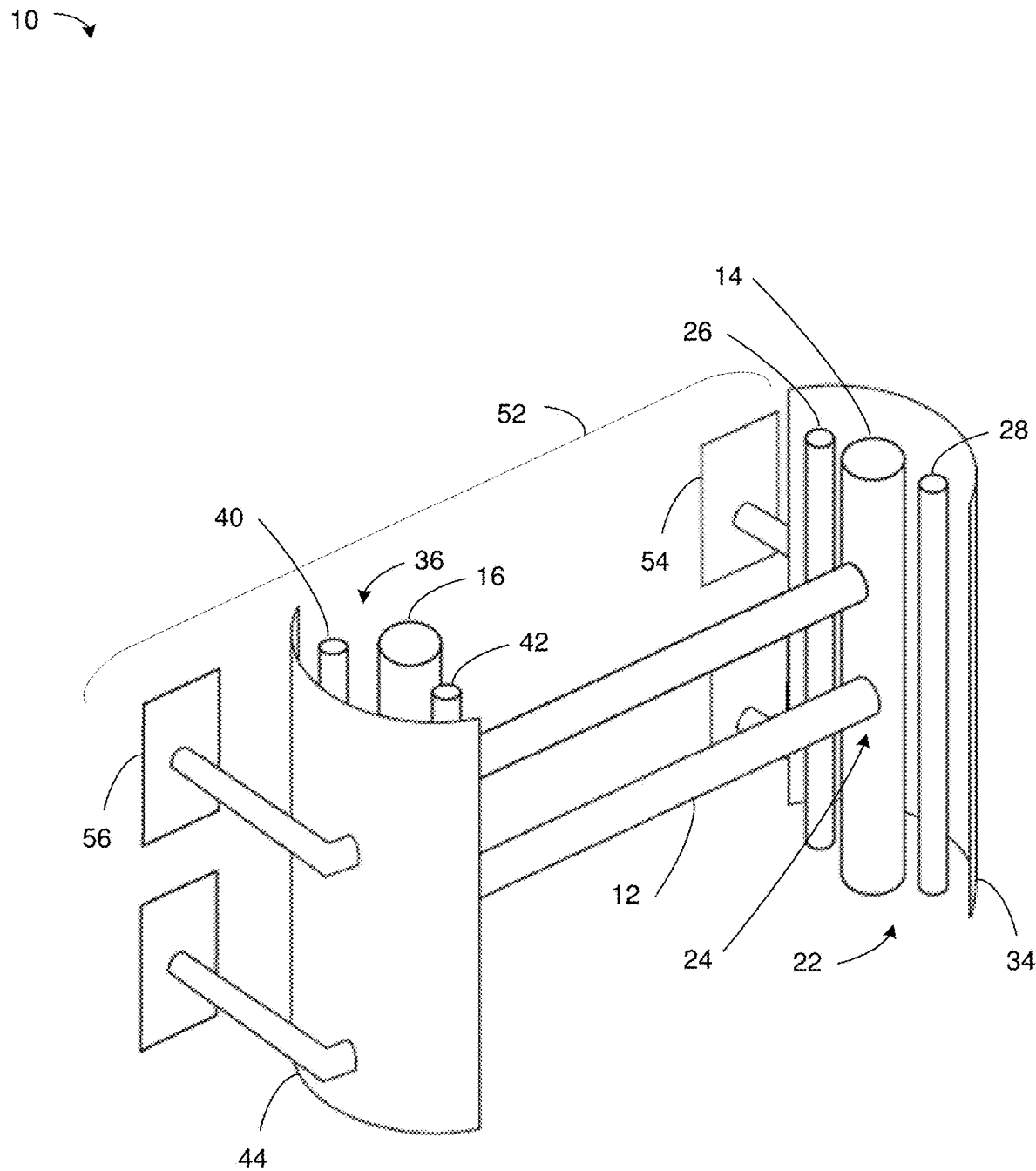
Figure 9:
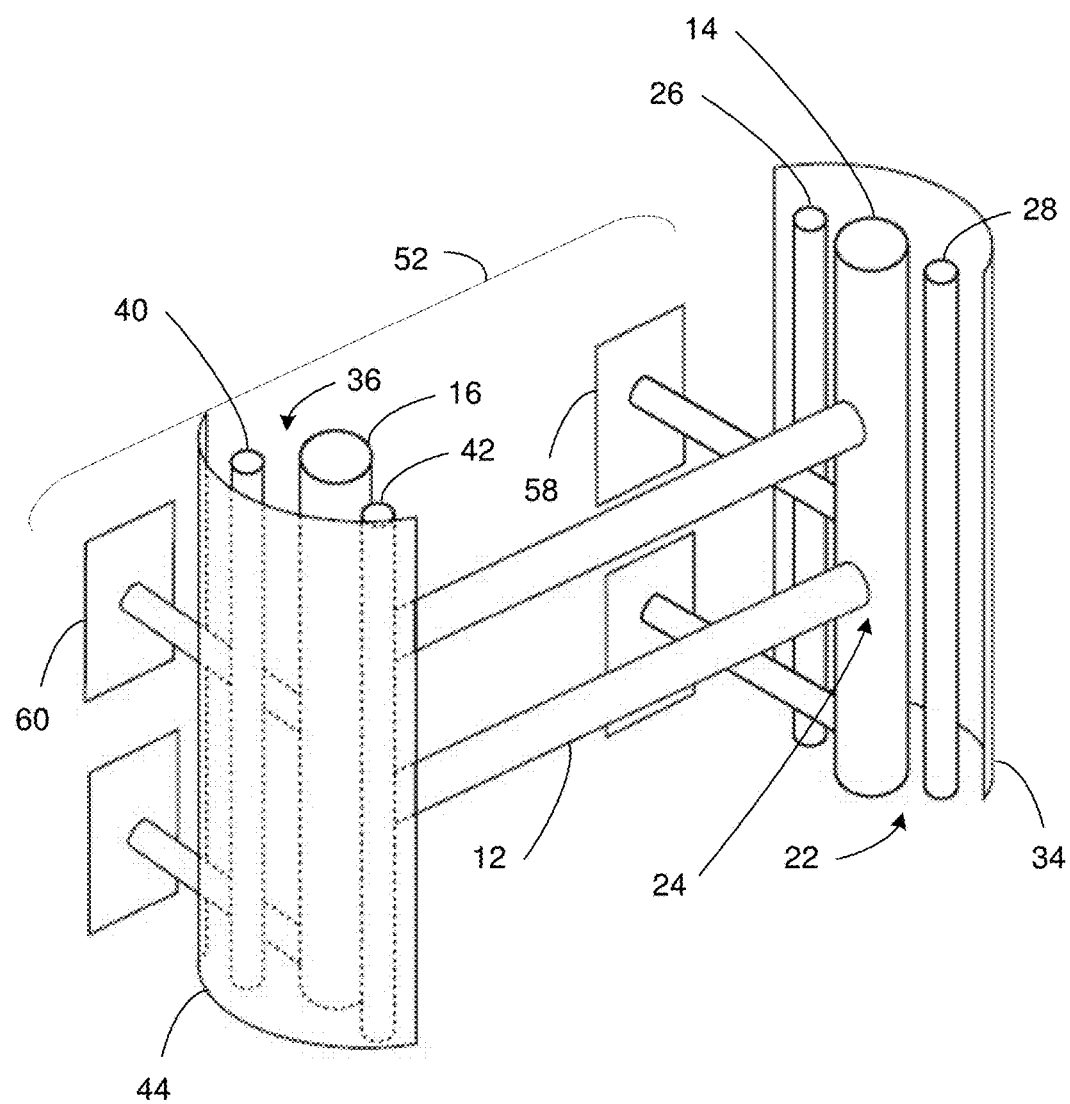

Referring also to the example of FIG. 7 and in some implementations, first wall-mounting subassembly 58 may be coupled to first support member 14 and second wall-mounting subassembly 60 may be coupled to the second support member 16. In these examples, fabric warming rack 10 may include a single rod. However, while examples of a fabric warming rack with a single rod and two wall-mounting subassemblies have been provided with various attachment points, it will be appreciated that any number of rods and any number of wall-mounting assemblies may be used within the scope of the present disclosure. For example and as shown in the example of FIG. 8, multiple wall-mounting assemblies may be coupled to each of the first reflector assembly and the second reflector assembly. As shown in the example of FIG. 9, multiple wall-mounting assemblies may be coupled to each of the first support member and the second support member. Accordingly, it will be appreciated that any number of rods and/or wall-mounting subassemblies may be used within the scope of the present disclosure.

In some implementations, the at least one rod (e.g., at least one rod 12) may be positioned between a first support member (e.g., first support member 14) and another structure (e.g., a wall or other structural component of a building). In some implementations, one of the first support member (e.g., first support member 14) and the second support member (e.g., second support member 16) may be ground-mounted and one of the first support member (e.g., first support member 14) and the second support member (e.g., second support member 16) may be wall-mounted.

Figure 10:
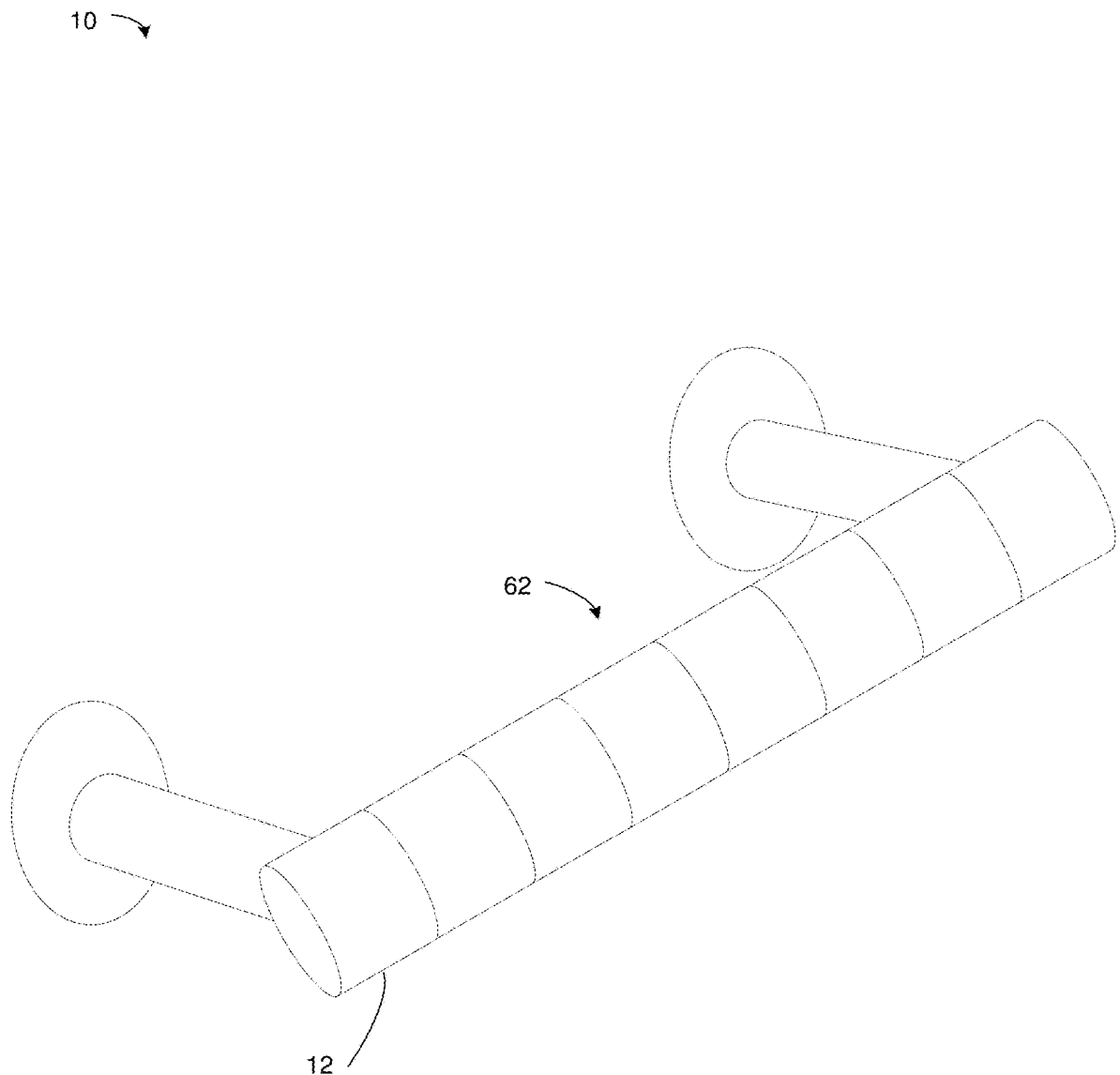
FIG. 10 is a diagrammatic view of a fabric warming rack with one or more light sources integrated into a rod.

In some implementations, fabric warming rack 10 may include at least one rod extending along a horizontal plane with one or more light sources integrated into the at least one rod. Referring also to the example of FIG. 10 and in some implementations, fabric warming rack 10 may include at least one rod (e.g., at least one rod 12) extending along a horizontal plane (e.g., as shown by arrow 18). In the example of FIG. 10, at least one rod 12 may include one or more light sources (e.g., one or more light sources 62) integrated into at least one rod 12. In some implementations and as discussed above, the one or more light sources 62 integrated into the at least one rod may include one or more ultraviolet (UV) light sources. In some implementations, one or more light sources 62 may form at least a portion of the at least one rod. For example, one or more light sources 62 may be configured in a cylindrical or tubular shape and configured to hold a fabric. In this manner, light may be emitted from one or more light sources 62 onto the interior surface of the fabric (e.g., surface of fabric draped over the at least one rod). In some implementations, one or more light sources 62 may be affixed or coupled to an exterior surface of at least one rod 12. In this example, light may be emitted from one or more light sources 62 affixed to the exterior surface of a fabric draped on at least one rod 12. As discussed above, one or more light sources 62 may be electrically coupled to a power source and/or power switch configured to activate the one or more light sources 62. In some implementations, one or more UV light sources integrated into at least one rod 12 may be configured to sanitize the interior surface of a fabric positioned on at least one rod 12.

Referring again to the example of FIGS. 1-2 and in some implementations, fabric warming rack 10 may include a plurality of rods. For example and in some implementations, one or more rods of the plurality of rods may include one or more light sources (e.g., one or more UV light sources) integrated within the one or more rods. In this example, these rods with integrated UV light sources may sanitize the internal surface of a fabric draped over the rods.

In some implementations, fabric warming rack may include a rod extending along a horizontal plane and a first light source rotatably coupled to the rod and configured to rotate about the rod. Referring also to the example of FIGS. 11-12B and in some implementations, fabric warming rack 10 may include a rod (e.g., a rod 12) extending along a horizontal plane or axis (e.g., horizontal plane or axis 18). In some implementations, fabric warming rack 10 may include a first light source (e.g., first light source 64) rotatably coupled to rod 12 and configured to rotate about rod 12. For example, first light source 64 may be coupled to rod 12 by coupling 66 configured to allow first light source 64 to rotate about rod 12. In some implementations, coupling 66 may allow first light source 64 to be rotated to any position about rod 12. In this manner, first light source 64 may be positioned at any angle relative to rod 12.

In one example, first light source 64 may be configured to emit light on a fabric draped on rod 12 from any angle. In some implementations, first light source 64 may be rotatably coupled to rod 12 via a combination of coupling 66 and rod 68. While reference is made to "a first" light source, it will be appreciated that multiple light sources may be rotatably coupled to the rod and configured to rotate about the rod. Accordingly, a plurality of light sources may be rotatably coupled to the rod along the length of the rod. In this manner, multiple light sources may be configured to emit light from various angles or orientations relative to the rod. In some implementations and as discussed above, the first light source may include one or more ultraviolet (UV) light sources. In this manner, first light source 64 may sanitize a fabric draped on rod 12 from various angles.

Figure 12A:
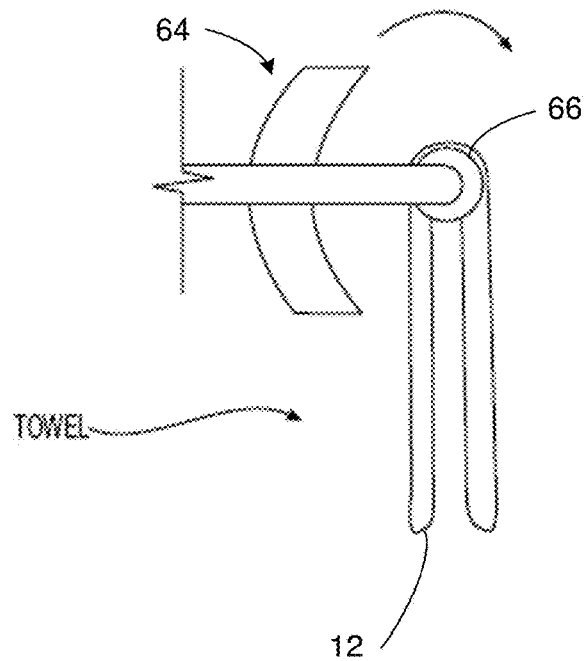
FIGS. 12A-12B are diagrammatic views of a fabric warming rack with a rotatable light source.
Figure 12B:
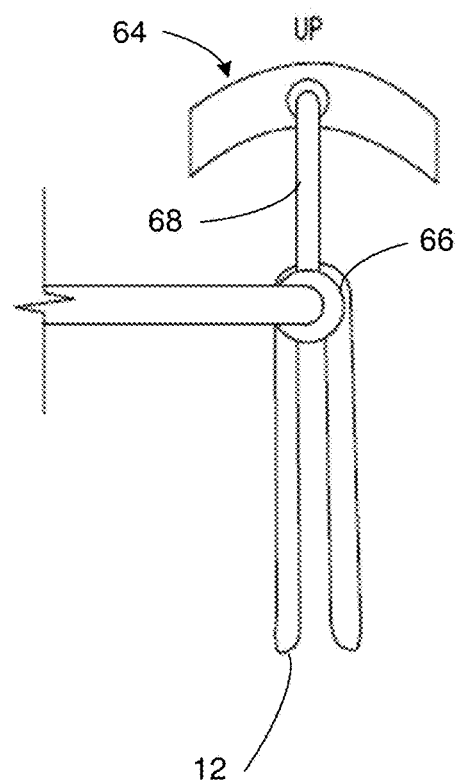

Referring again to the examples of FIGS. 12A-12B, first light source 64 may be rotated into a first position (as shown in FIG. 12A) to allow a user to access rod 12 from above rod 12 (e.g., to place a fabric on rod 12). Once a fabric is positioned on rod 12, first light source 64 may be rotated to any angle relative to rod 12. In the example of FIG. 12B, first light source 64 may be rotated to emit light from "above" a fabric and along the length of the fabric.

Figure 11:
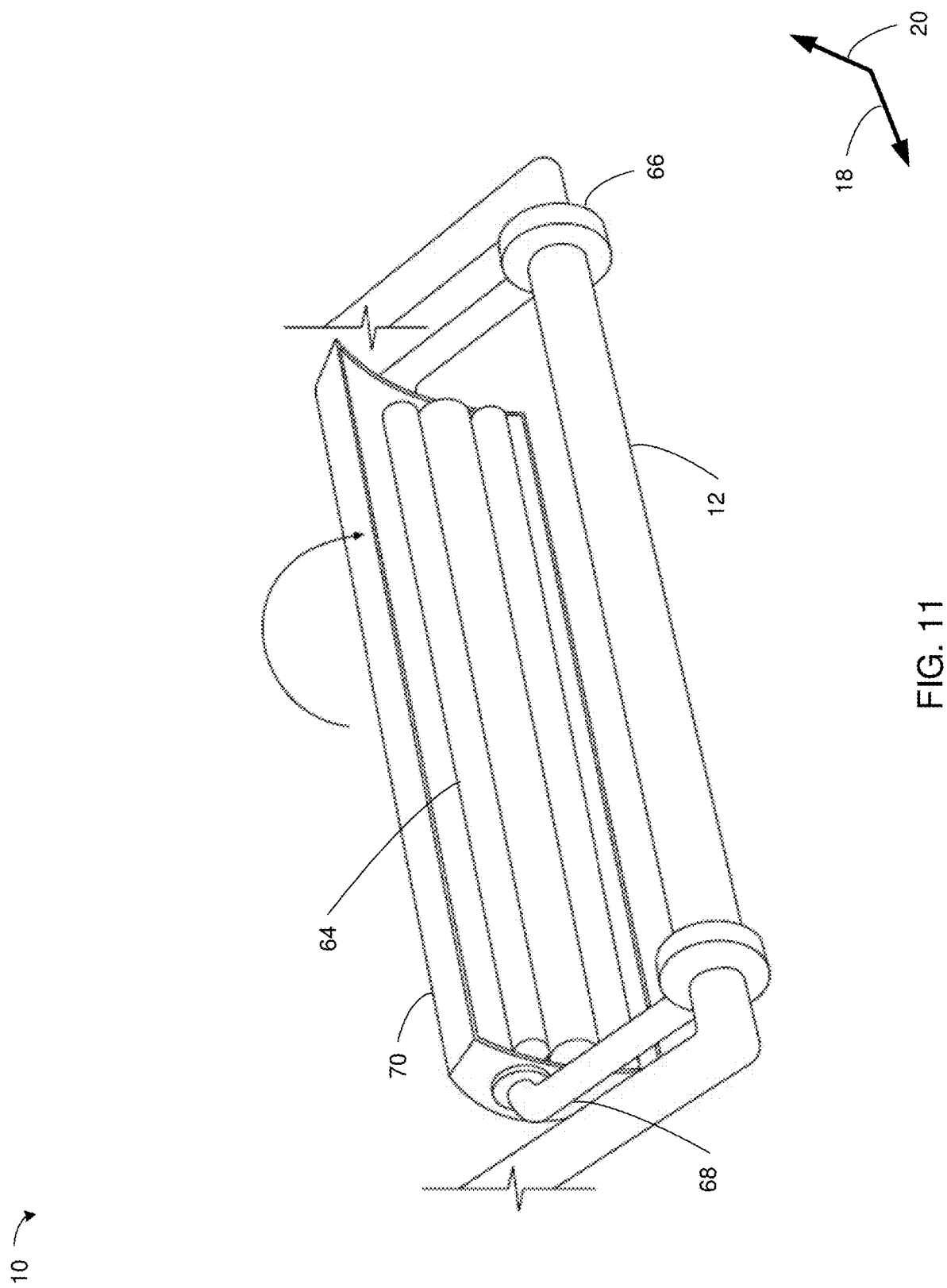
FIG. 11 is a diagrammatic view of a fabric warming rack with a rotatable light source.

In some implementations, fabric warming rack 10 may include a first reflector assembly rotatably coupled to the rod and configured to reflect at least a portion of light emitted by the first light source toward the rod. For example, a first reflector assembly (e.g., first reflector assembly 70) may be coupled to rod 68 and configured to rotate about rod 12. In some implementations, first reflector assembly 70 may be configured to reflect at least a portion of light emitted by the first light source (e.g., first light source 64) toward rod 12. In the examples of FIGS. 11-12B, first reflector assembly 70 may be a curved metal or other material known in the art that is configured to reflect light emitted from first light source 64 back to rod 12. While in this example, first reflector assembly 70 may be curved, it will be appreciated that first reflector assembly 70 may be configured in various shapes and forms within the scope of the present disclosure. As shown in the example of FIG. 11, light emitted by first light source 64 may be either directly emitted or reflectively emitted toward rod 12. In this manner, fabric warming rack 10 may allow fabrics to be evenly warmed and sanitized.

Figure 13A:
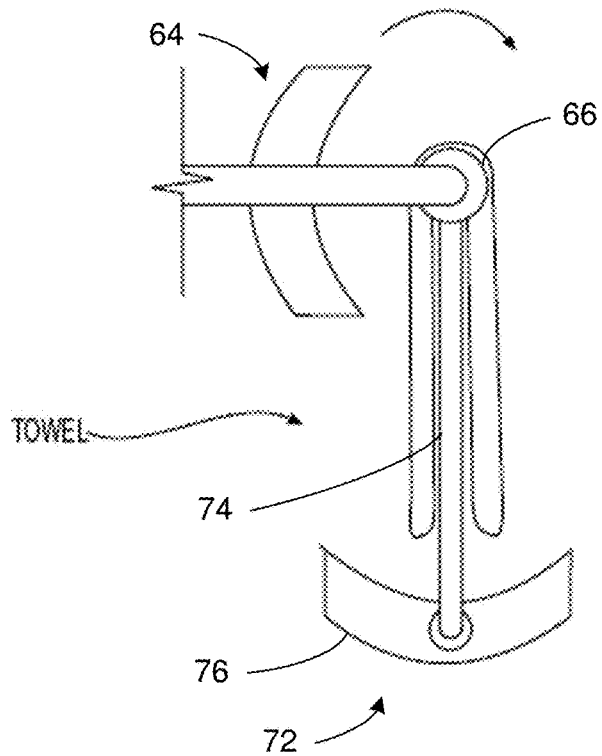
FIGS. 13A-13B are diagrammatic views of a fabric warming rack with a rotatable light source and a second light source positioned at a fixed vertical distance from a rod.
Figure 13B:
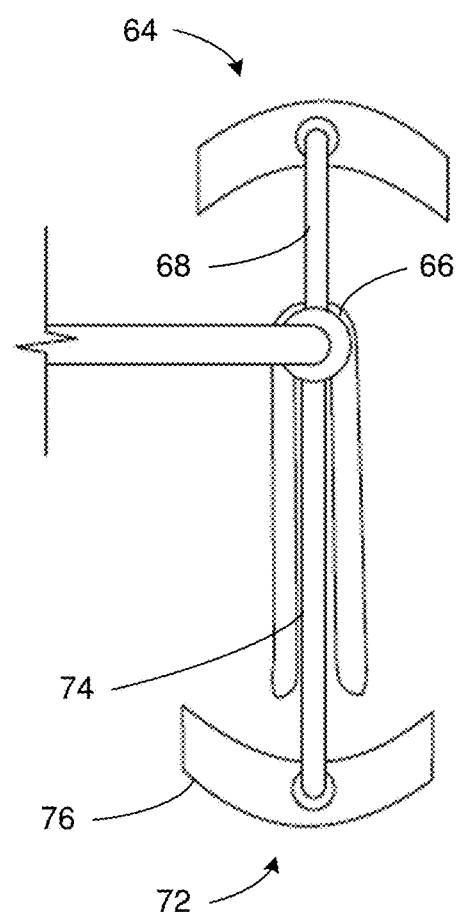

In some implementations, fabric warming rack 10 may include a second light source positioned at a fixed vertical distance from the rod. Referring also to the examples of FIGS. 13A-13B and in some implementations, fabric warming rack 10 may include a second light source (e.g., second light source 72) positioned at a fixed vertical distance from the rod. In some implementations, second light source 72 may be coupled to rod 12 via a fixed length of rod (e.g., vertical distance rod 74). In some implementations and as shown in the examples of FIG. 13A-13B, second light source 72 may be positioned at a fixed vertical distance from rod 12 via vertical distance rod 74. In some implementations, second light source 72 may be configured to emit light from beneath a draped fabric. In this manner and as shown in the example of FIG. 13B, the combination of first light source 64 and second light source 72 may be configured to emit light along the entire length (e.g., from top to bottom) of a fabric draped on rod 12.

In some implementations, fabric warming rack 10 may include a second reflector assembly rotatably coupled to the rod and configured to reflect at least a portion of light emitted by the second light source toward the rod. For example, a second reflector assembly (e.g., second reflector assembly 76) may be coupled to rod 74. In some implementations, second reflector assembly 76 may be configured to reflect at least a portion of light emitted by the second light source (e.g., second light source 72) toward rod 12. In the examples of FIGS. 13A-13B, second reflector assembly 76 may be a curved metal or other material known in the art that is configured to reflect light emitted from second light source 72 back to rod 12. While in this example, second reflector assembly 76 may be curved, it will be appreciated that second reflector assembly 76 may be configured in various shapes and forms within the scope of the present disclosure. As shown in the example of FIGS. 13A-13B, light emitted by second light source 72 may be either directly emitted or reflectively emitted toward rod 12. In this manner, fabric warming rack 10 may allow fabrics to be evenly warmed and sanitized.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A fabric warming rack comprising:
a rod extending along a horizontal plane; and
a first light source rotatably coupled to the rod and configured to rotate about the rod, wherein the first light source includes a pair of rods rotatably coupled to the rod on respective ends of the first light source that are configured to position the first light source at a fixed distance from the rod while orienting the first light source to emit light toward the rod.

2. The fabric warming rack of claim 1, wherein the first light source includes one or more ultraviolet (UV) light sources.

3. The fabric warming rack of claim 1, further comprising:
a first reflector assembly rotatably coupled to the rod and configured to reflect at least a portion of light emitted by the first light source toward the rod.

4. The fabric warming rack of claim 1, further comprising:
a second light source positioned on a first end of the rod; and
a third light source positioned on a second end of the rod.

5. The fabric warming rack of claim 4, wherein the second light source extends along a vertical plane relative to the rod.

6. The fabric warming rack of claim 4, wherein the third light source extends along a vertical plane relative to the rod.

7. The fabric warming rack of claim 4, wherein the second light source includes one or more ultraviolet (UV) light sources.

8. The fabric warming rack of claim 4, wherein the third light source includes one or more ultraviolet (UV) light sources.

9. The fabric warming rack of claim 4, further comprising:
a first reflector assembly positioned on the first end of the rod and configured to reflect at least a portion of light emitted by the first light source toward the rod.

10. The fabric warming rack of claim 4, further comprising:
a second reflector assembly positioned on the second end of the rod and configured to reflect at least a portion of light emitted by the second light source toward the rod.

11. The fabric warming rack of claim 1, further comprising one or more of:
a wall-mounting assembly; and
a ground-mounting assembly.

12. The fabric warming rack of claim 1, wherein the fabric warming rack is unenclosed.

13. A fabric warming rack comprising:
a rod extending along a horizontal plane;
a first light source rotatably coupled to the rod and configured to rotate about the rod, wherein the first light source includes a pair of rods rotatably coupled to the rod on respective ends of the first light source that are configured to position the first light source at a fixed distance from the rod while orienting the first light source to emit light toward the rod; and
a second light source includes a pair of rods rotatably coupled to the rod on respective ends of the second light source that are configured to position the second light source at a fixed vertical distance below the rod.

14. The fabric warming rack of claim 13, wherein at least one of the first light source and the second light source includes one or more ultraviolet (UV) light sources.

15. The fabric warming rack of claim 13, further comprising:
a first reflector assembly rotatably coupled to the rod and configured to reflect at least a portion of light emitted by the first light source toward the rod.

16. The fabric warming rack of claim 13, further comprising:
a second reflector assembly rotatably coupled to the rod and configured to reflect at least a portion of light emitted by the second light source toward the rod.

17. The fabric warming rack of claim 13, further comprising:
a third light source positioned on a first end of the rod; and
a fourth light source positioned on a second end of the rod.

18. The fabric warming rack of claim 17, wherein the third light source extends along a vertical plane relative to the rod.

19. The fabric warming rack of claim 17, wherein the fourth light source extends along a vertical plane relative to the rod.

20. The fabric warming rack of claim 13, further comprising one or more of:
a wall-mounting assembly; and
a ground-mounting assembly.

* * * * *